(12) United States Patent
Kato et al.

(10) Patent No.: US 12,257,400 B2
(45) Date of Patent: Mar. 25, 2025

(54) MEDICAL APPARATUS WITH REFLOW TRAPPED ANCHORS AND METHOD OF USE THEREOF

(71) Applicant: Canon U.S.A., Inc., Melville, NY (US)

(72) Inventors: Takahisa Kato, Brookline, MA (US); Matthew Michael Kincaid, Medford, MA (US); Showna Hsu-Hwa Chang, Arlington, MA (US)

(73) Assignee: Canon U.S.A., Inc., Melville, NY (US)

( * ) Notice: Subject to any disclaimer, the term of this patent is extended or adjusted under 35 U.S.C. 154(b) by 1007 days.

(21) Appl. No.: 17/288,329

(22) PCT Filed: Oct. 23, 2019

(86) PCT No.: PCT/US2019/057706
§ 371 (c)(1),
(2) Date: Apr. 23, 2021

(87) PCT Pub. No.: WO2020/092097
PCT Pub. Date: May 7, 2020

(65) Prior Publication Data
US 2021/0369085 A1 Dec. 2, 2021

Related U.S. Application Data

(60) Provisional application No. 62/753,648, filed on Oct. 31, 2018.

(51) Int. Cl.
*A61M 25/01* (2006.01)
*A61B 1/005* (2006.01)
(Continued)

(52) U.S. Cl.
CPC ....... *A61M 25/0113* (2013.01); *A61B 1/0057* (2013.01); *A61B 1/008* (2013.01);
(Continued)

(58) Field of Classification Search
CPC .... A61M 25/0113; A61B 34/20; A61B 34/30; A61B 90/37; A61B 1/0057; A61B 1/008; A61B 1/012
(Continued)

(56) References Cited

U.S. PATENT DOCUMENTS 5,368,564 A 11/1994 Savage
5,916,147 A * 6/1999 Boury ............... A61M 25/0147
600/149

(Continued)

FOREIGN PATENT DOCUMENTS

JP S6150545 A 3/1986
JP H05154091 A 6/1993
(Continued)

*Primary Examiner* — Phillip A Gray
(74) *Attorney, Agent, or Firm* — Canon U.S.A., Inc., IP Division

(57) ABSTRACT

An articulated medical device having a hollow core, capable of large degrees of maneuverability through small spaces of a patient to reach a target with minimal invasiveness, and once the medical device has reached the target, allowing a medical tool to be guided through the hollow chamber for facilitating medical procedures, including endoscopes, cameras, and catheters, at the target.

19 Claims, 6 Drawing Sheets

(51) Int. Cl.
    *A61B 1/008*      (2006.01)
    *A61B 1/012*      (2006.01)
    *A61B 34/20*      (2016.01)
    *A61B 34/30*      (2016.01)
    *A61B 90/00*      (2016.01)
    *A61M 25/00*      (2006.01)
    *A61M 25/09*      (2006.01)

(52) U.S. Cl.
    CPC .............. *A61B 1/012* (2013.01); *A61B 34/20* (2016.02); *A61B 34/30* (2016.02); *A61B 90/37* (2016.02); *A61M 25/0026* (2013.01); *A61M 25/0053* (2013.01); *A61M 25/0102* (2013.01); *A61M 25/0105* (2013.01); *A61M 25/0141* (2013.01); *A61M 25/0147* (2013.01); *A61B 1/005* (2013.01); *A61B 2034/2074* (2016.02); *A61B 2034/301* (2016.02); *A61B 2090/374* (2016.02); *A61B 2090/3762* (2016.02); *A61M 2025/0063* (2013.01); *A61M 2025/0166* (2013.01); *A61M 2025/0915* (2013.01)

(58) Field of Classification Search
    USPC ........................................................ 604/528
    See application file for complete search history.

(56) References Cited

U.S. PATENT DOCUMENTS

| | | |
|---|---|---|
| 9,155,449 B2 | 10/2015 | Danitz et al. |
| 2002/0177766 A1 | 11/2002 | Mogul |
| 2006/0074383 A1 | 4/2006 | Boulais |
| 2007/0225701 A1 | 9/2007 | O'Sullivan |
| 2011/0152880 A1 | 6/2011 | Alvarez et al. |
| 2013/0090529 A1* | 4/2013 | Boulais ................ A61B 1/0016 600/149 |
| 2014/0121641 A1* | 5/2014 | Fischell ............ A61M 25/0108 604/102.03 |
| 2017/0231473 A1 | 8/2017 | Ostrovsky et al. |

FOREIGN PATENT DOCUMENTS

| | | |
|---|---|---|
| JP | 2002360704 A | 12/2002 |
| JP | 2015163128 A | 9/2015 |
| JP | 2016002226 A | 1/2016 |
| JP | 2016538031 A | 12/2016 |
| JP | 2018140101 A | 9/2018 |
| JP | 2018140102 A | 9/2018 |
| WO | 2017/155892 A1 | 9/2017 |
| WO | 2020/243285 A1 | 12/2020 |

* cited by examiner

MEDICAL APPARATUS WITH REFLOW TRAPPED ANCHORS AND METHOD OF USE THEREOF

CROSS REFERENCE TO RELATED PATENT APPLICATIONS

This application claims priority to U.S. Provisional Patent Application No. 62/753,648, titled "Medical Apparatus with Reflow Trapped Anchors and Method of Use Thereof" filed on Oct. 31, 2018, the disclosure of which is herein incorporated in its entirety by reference.

FIELD OF THE DISCLOSURE

The present disclosure relates generally to apparatus and methods for medical application. More particularly, the subject disclosure is directed to an articulated medical device having a hollow chamber, wherein the device is capable of maneuvering within a patient, and allowing a medical tool to be guided through the hollow chamber for medical procedures. The medical tool may include an endoscope, camera catheters or other tools.

BACKGROUND OF THE DISCLOSURE

Bendable medical instruments such as endoscopic surgical instruments and catheters are well known and continue to gain acceptance in the medical field. The bendable medical instrument generally includes a flexible body commonly referred to as a sleeves or sheaths. One or more tool channels extend along (typically inside) the flexible body to allow access to a target located at a distal end of the body.

The instrument is intended to provide flexible access within a patient, with at least one curve or more leading to the intended target, while retaining torsional and longitudinal rigidity so that a physician can control the tool located at the distal end of the medical instrument by maneuvering the proximal end of the instrument.

Recently, to enhance maneuverability of the distal end of the instrument, robotized instruments that control distal portions have emerged. In those robotized instruments, to create curves locally at the distal portion by robotics, different techniques have been disclosed.

By way of example, United States patent publication number 2016/0067450, provides multiple conduits to retain the shape of the proximal part, while the driving tendons are bending the distal part in the medical instruments. The multiple conduits would be controlled selectively in a binary way by constraining or unconstraining the proximal ends of the conduits. By selecting the constrained conduits, the bendable medical device can change the length of bending distal segment by changing the stiffness of the bendable medical device based on the area where the conduits deploy However, there remains a need in the industry to further refine and advance bendable medical devices to minimize the outer size (diameter) of the bendable medical instrument, and to maximize the size (diameter) of the tool channel, allowing for larger/more effective tools.

SUMMARY

Thus, to address such exemplary needs in the industry, the presently disclosed apparatus teaches a medical apparatus comprising: A medical apparatus comprising a bendable body having a hollow chamber extending the length of the bendable body, at least two guide rings disposed collectively in the bendable body and spaced a distance from one another to create a cavity, at least two lumens in the bendable body extending the length of the bendable body and parallel with the hollow chamber, at least one control wire slideably situated in the lumen and attached to a distal end of the bendable body, and a wall extending the length of the bendable body and configured to be in contact with the at least two guide rings, wherein the wall is pliable to allow for bending of the bendable body without kinking.

In one embodiment, the wall defines the hollow cavity and is in contact with an inner diameter of the guide rings. Whereas another embodiment teaches the wall in contact with the outer diameter of the guide rings, so as to encapsulate the bendable body. While a third embodiment may employ the wall to both define the hollow cavity and is in contact with an inner diameter of the guide rings, as well contact the outer diameter of the guide rings so as to encapsulate the bendable body.

In another embodiment, the bendable body has a first bendable section and a second bendable section, wherein the at least two guide rings are disposed in the first bendable section.

In yet another embodiment, the at least two guide rings are attached to at least a portion of the wall. Furthermore, the wall may comprise a resilient outer lining and a resilient inner lining for encapsulating the at least two rings, wherein the inner lining may define the hollow chamber.

In additional embodiments, the apparatus may comprise an actuator attached to a proximal end of the at least one control wire, wherein the actuator is configured to actuate the control wire.

Another embodiment of the subject innovation may include a support wire slideably situated in the at least one lumen. In some variants, the support wire is slideably situated in the lumen of at least one guide ring.

In other embodiment, the support wire is attached to the bendable body at a distal end of the support wire. Furthermore, the support wire may extend through at least two lumens, where the at least two lumens are parallel to the hollow chamber.

In yet additional embodiments, a plurality of support wires may be configured around the hollow chamber, and be capable of free movement while the apparatus is manipulated.

Additional embodiments may include a second control wire slideably situated in the lumen and attached to the bendably body, wherein the position of attachment for the first and the second control wires are different along the axial direction of the bendable body.

In various embodiments, the at least two lumens extend through the at least two guide rings.

In yet additional embodiments, the control wire and lumen comprise of a radio opaque material.

In addition, the subject application teaches a medical apparatus comprising: a bendable body having a first bending section and a second bending section, with the first bending section in a position distal to the second bending section; a first control wire connected to a distal end of the first bending section; a second control wire connected to a distal end of the second bending section; at least two lumens in the bendable body extending the length of the bendable body through both the first bending section and second bending section; wherein the first bending section comprises: at least two guide rings disposed in the bendable body and spaced a distance from one another to create a cavity; and a wall extending the length of the first bending section and configured to encapsulated the at least two guide rings, wherein the wall comprises a resilient outer lining and a resilient inner lining for encapsulating the at least two rings, wherein the first control wire is slideably situated in the lumen of the first bending section and the second control wire is situated in the lumen of the second bending section, and wherein the wall is pliable to allow for bending of the bendable body without kinking.

The subject application also teaches a medical apparatus comprising: a bendable body having a hollow chamber extending the length of the bendable body; at least two guide rings disposed collectively in the bendable body and spaced a distance from one another to create a cavity; at least two lumens in the bendable body extending the length of the bendable body and parallel with the hollow chamber; at least one control wire slideably situated in the lumen and attached to a distal end of the bendable body, and a wall extending the length of the bendable body and attached to the at least two guide rings, wherein the wall is pliable to allow for bending of the bendable body without kinking.

Further embodiments taught the subject application include a method for treating a subject, comprising: providing a medical apparatus comprising: a bendable body having a hollow chamber extending the length of the bendable body; at least two guide rings disposed collectively in the bendable body and spaced a distance from one another to create a cavity; at least two lumens in the bendable body extending the length of the bendable body and parallel with the hollow chamber; at least one control wire slideably situated in the lumen and attached to a distal end of the bendable body, and a wall extending the length of the bendable body and configured to encapsulated the at least two guide rings, wherein the wall is pliable to allow for bending of the bendable body without kinking; the treatment further comprising: advancing the medical apparatus into a subject; bending the medical apparatus to accommodate obstacles in the subject; and treating the subject once the medical apparatus advances to a desired target in the subject.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

FIG. 8b provides a photograph of a prior art bendable medical device, as a comparison for FIG. 8a.

Figure 1:
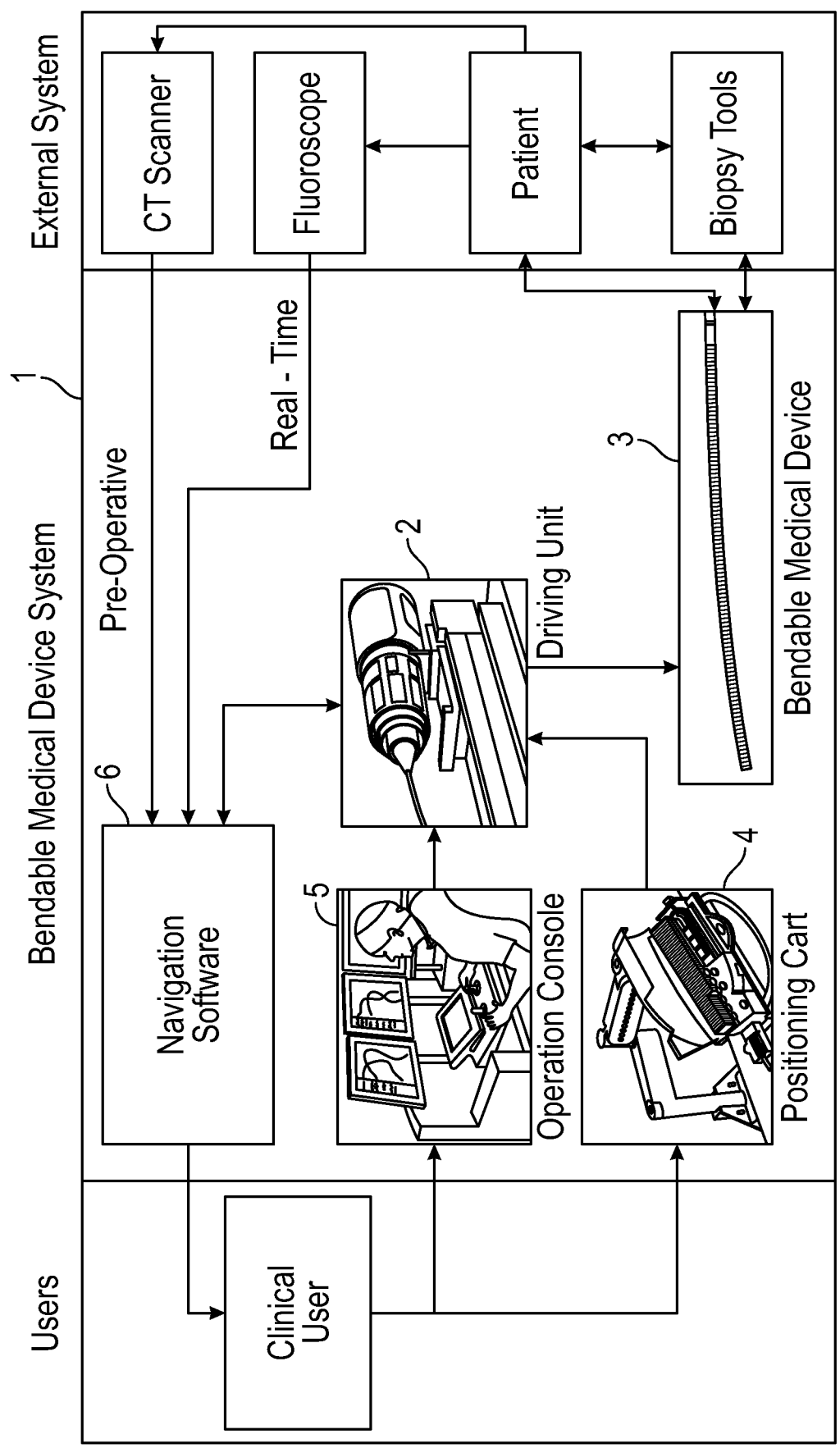
FIG. 1 is a block diagram of an exemplary bendable medical device incorporating various ancillary components, according to one or more embodiment of the subject apparatus, method or system.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify secondary elements and/or references of the same nature and/or kind. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION OF THE DISCLOSURE

FIG. 1 is a system block diagram of an exemplary bendable medical device system 1 incorporating various ancillary components intended to amass a complete medical system. The bendable medical device system 1 comprises a driving unit 2, a bendable medical device 3, a positioning cart 4, an operation console 5 and navigation software 6. The exemplary bendable medical device system 1 is capable of interacting with external system component and clinical users to facilitate use in a patient.

The navigation software 6 and the driving unit 2 are communicatively-coupled via a bus to transmit/receive data between each other. Moreover, the navigation software 6 is connected and may communicate with a CT scanner, a fluoroscope and an image server (not in Figure), which are ancillary components of the bendable medical device system 1. The image server may include, but is not limited to, a DICOM™ server connected to a medical imaging device including but not limited to a CT and/or MRI scanner and a fluoroscope. The navigation software 6 processes data provided by the driving unit 2 and data provided by images stored on the image server, and/or images from the CT scanner and the fluoroscope in order to display images onto the image display.

The images from the CT scanner may be pre-operatively provided to navigation software 6. With navigation software, a clinical user creates an anatomical computer model from the images. In this particular embodiment, the anatomy is that of a lung with associated airways. From the chest images of the CT scanner, the clinical user can segment the lung airways for clinical treatments, such as biopsy. After generating the lung airway map, the user can also create plan to access the lesion for the biopsy. The plan includes the airways to insert and maneuver the bendable medical device 3 leading to the intended target, which in this example is a lesion.

The driving unit 2 comprises actuators and a control circuitry. The control circuitry is communicatively-coupled with operation console 5. The driving unit 2 is connected to the bendable medical device 3 so that the actuators in the driving unit 2 operate the bendable medical device 3. Therefore, a clinical user can control the bendable medical device 3 via the driving unit 2. The driving unit 2 is also physically connected to a positioning cart 4. The positioning cart 4 includes a positioning arm, and locates the driving unit 2 and the bendable medical device 3 in the intended position with respect to the target/patient. The clinical user can insert, maneuver and retreat the bendable medical device 3 to perform medical procedures, here a biopsy in the lungs of the patient.

The bendable medical device 3 can be navigated to the lesion in the airways based on the plan by the clinical user's operation. The bendable medical device 3 includes a hollow chamber for various tools (e.g. a biopsy tool). The bendable medical device 3 can guide the tool to the lesion of the patient. In one example, the clinical user can take a biopsy sample from the lesion with a biopsy tool.

Figure 2:
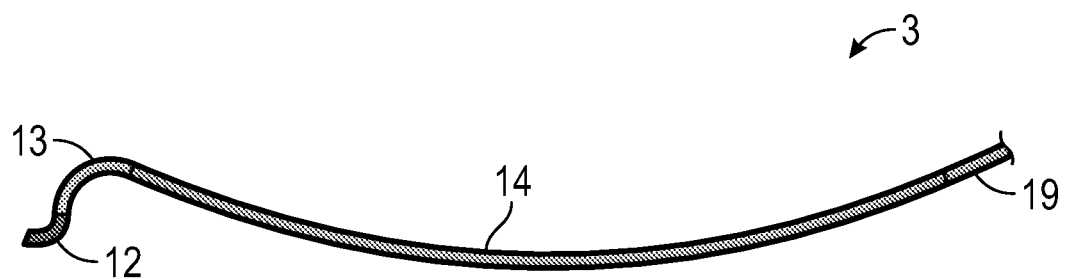
FIG. 2 depicts a perspective view of an exemplary bendable medical device, according to one or more embodiment of the subject apparatus, method or system.

FIG. 2 is a schematic drawing to explain the bendable segments of the bendable medical device 3. The bendable medical device 3 comprises a proximal part 19 and three bendable segments, which are the first, second, and third bendable segments 12, 13, 14, respectively. The bendable segments 12, 13, 14, can independently bend and can form a shape with three independent curvatures, as seen in FIGS. 4 and 5.

Figure 3A:
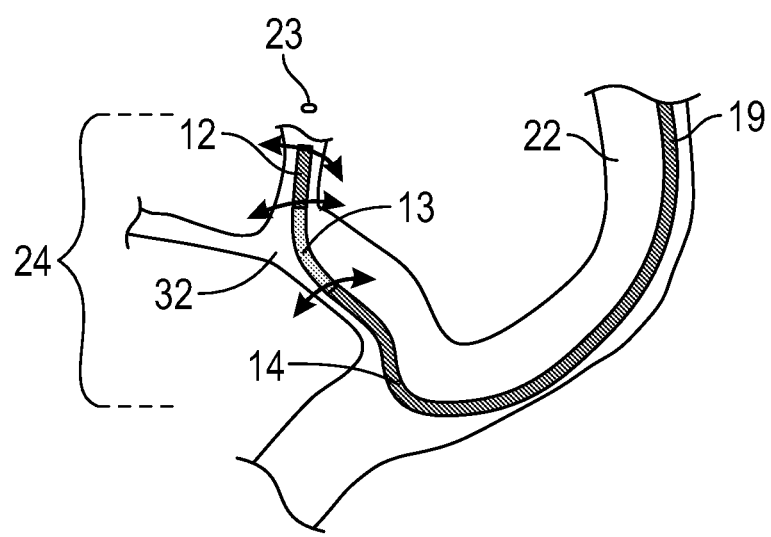
FIG. 3a provides a cut-away view of an exemplary bendable medical device inserted into a patient, according to one or more embodiment of the subject apparatus, method or system.

FIG. 3a provides a cut-away view of an exemplary bendable medical device 3 inserted into a patient, specifically, the peri-bronchial area of a patient's lungs, which is a lateral area surrounding the airways. This area is a known challenge to target as identified in literature, and the prior art, due to the limited distal dexterity of the conventional catheter. To reach the lesion through airways 22 in the navigation stage, the first and the second bendable segments 12, 13, respectively, navigate the bendable medical device 3 through the bifurcation point 32. The first bendable segment 12 can adjust the shape/orientation to the daughter branch while the second bendable segment 13 can adjust the shape/orientation to the parent branch in the bifurcation point 32, as the bendable medical device 3 advances through the bifurcation point 32. Once the first and the second bendable segments 12 and 13 pass the bifurcation point 32, those segments may act as guides for the rest of the bendable medical device 3, so that the insertion force from the proximal end of the bendable medical device 3 can be effectively transformed into the insertion force for a distal part of the bendable medical device 3 without serious prolapsing of the distal section. Once the distal end 24 of the bendable medical device 3 reaches the vicinity of the lesion 23, the bendable medical device 3 would direct the distal end 24 to the lesion 23, which locates the lateral area around the airway, by bending the first and the second bendable segments 12 and 13, respectively. Since the airway doesn't directly connect with the lesion 23, this is one of the more difficult configurations for a conventional catheter.

With the first, the second and the third bendable segments 12, 13 and 14, respectively, the bendable medical device 3 can orient the distal end 24 without moving the proximal part 19 that goes through all bifurcations to this lesion 23. By using the three-dimensional bending capability of the first and the second bendable segments 12 and 13, the bendable medical device 3 can perform unique maneuvers to enhance capability of the peri-bronchial targeting. Therefore, the bendable medical device 3 can provide improved access to the intended lesion 23 through tortuous pathways. Also, the bendable medical device 3 can have different flexibility along the axial direction without increasing the size or number of the jointing points.

Figure 3B:
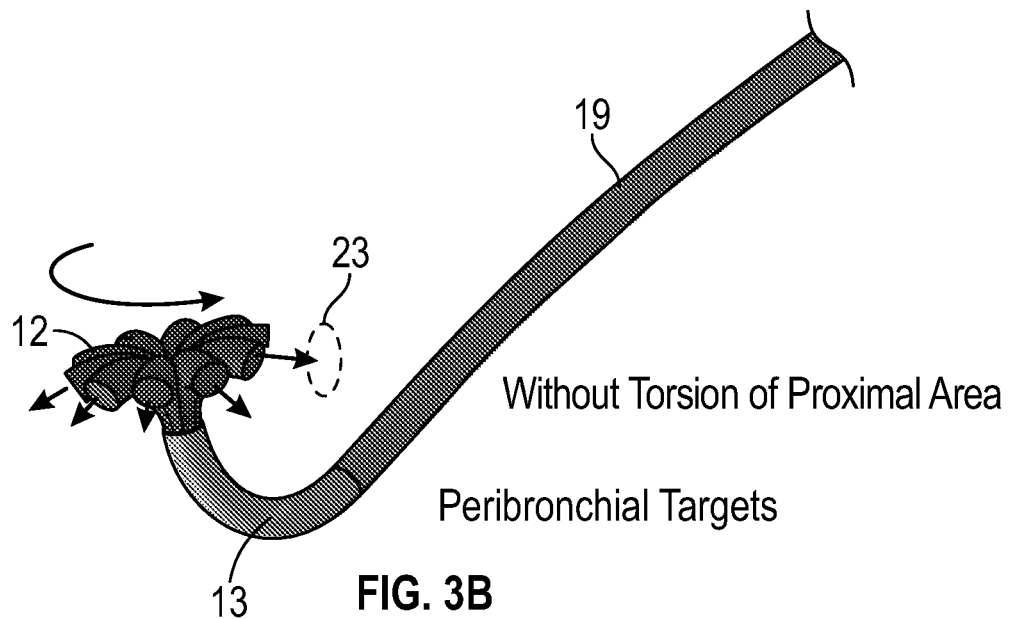
FIG. 3b provides a perspective view of an exemplary bendable medical device depicting various orientation options, according to one or more embodiment of the subject apparatus, method or system.
Figure 3C:
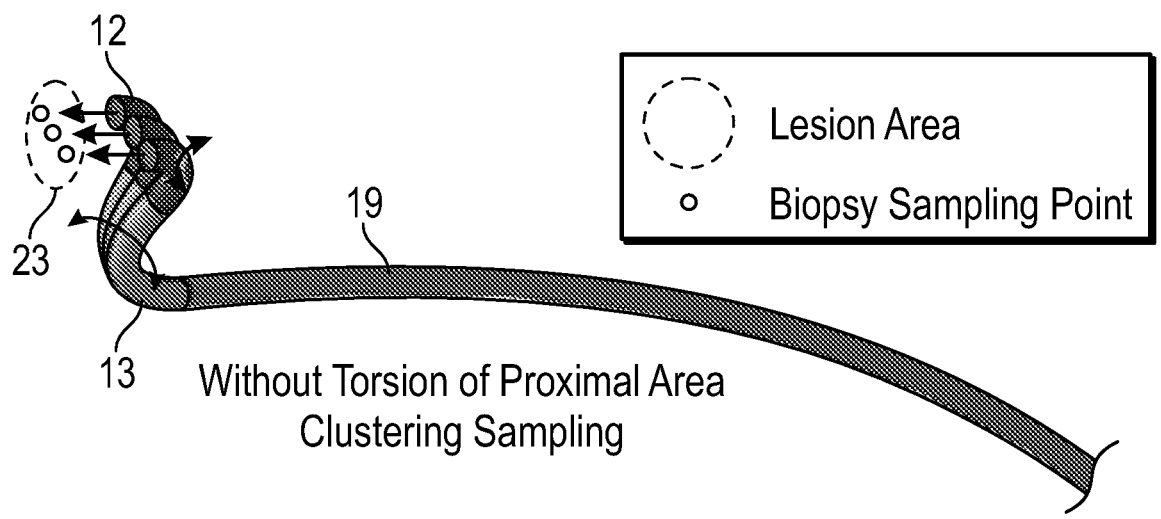
FIG. 3c depicts a perspective view of an exemplary bendable medical device depicting various orientation options, according to one or more embodiment of the subject apparatus, method or system.

FIG. 3a provides a cut-away view of an exemplary bendable medical device 3 inserted into a patient, wherein FIGS. 3b and 3c provide perspective views of an exemplary bendable medical device 3 depicting various orientation/maneuvering options.

FIGS. 3a, 3b and 3c are schematic drawings to explain the navigation and targeting of a lesion in peri-bronchial area of a patient's lungs, which is a lateral area surrounding the airways. This area is a known challenge to target as identified in literature, and the prior art, due to the limited distal dexterity of the conventional catheter. To reach the lesion through airways 22 in the navigation stage, the first and the second bendable segments 12, 13, respectively, navigate the bendable medical device 3 through the bifurcation point 32. The first bendable segment 12 can adjust the shape/orientation to the daughter branch while the second bendable segment 13 can adjust the shape/orientation to the parent branch in the bifurcation point 32, as the bendable medical device 3 advances through the bifurcation point 32. Once the first and the second bendable segments 12 and 13 pass the bifurcation point 32, those segments may act as guides for the rest of the bendable medical device 3, so that the insertion force from the proximal end of the single catheter can be effectively transformed into the insertion force for a distal part of the single catheter without serious prolapsing of the distal section. Once the distal end 24 of the bendable medical device 3 reaches the vicinity of the lesion, the bendable medical device 3 would direct the distal end 24 to the lesion 23, which locates the lateral area around the airway, by bending the first and the second bendable segments 12 and 13, respectively. Since the airway doesn't directly connect with the lesion 23, this is one of the more difficult configurations for a conventional catheter.

With the first, the second and the third bendable segments 12, 13 and 14, respectively, the bendable medical device 3 can orient the distal end 24 without moving the proximal part 19 that goes through all bifurcations to this lesion. By using the three-dimensional bending capability of the first and the second bendable segments 12 and 13, the bendable medical device 3 can perform unique maneuvers to enhance capability of the peri-bronchial targeting (FIGS. 3b, 3c). Furthermore, by incorporating different positions for the anchors 21 between the first 9, second 10 and third 11 control wires along the axial direction of the bendable body 7, the bendable body 7 can function as different bending segments along the axial direction, because the control wires 9, 10, 11, are mapped to the different position of the bendable body 7. Therefore, the bendable medical device 3 can provide improved access to the intended lesion through tortuous pathways. Also, the bendable medical device 3 can have different flexibility along the axial direction without increasing the size or number of the jointing points.

In a first maneuver in an omni-directional orientation (FIG. 3b), the first bendable segment 12 can effectively rotate without rotating any part of the bendable medical device 3. This maneuver is beneficial to determine the orientation of the distal end to the lesion 23 since this motion isn't affected by the physical interaction of the proximal part of the catheter to the anatomy, as well as not affecting the position of lesion 23, while physically mapping the orientation of the distal end 24. Moreover, with the second bendable segment 13, the bendable medical device 3 can perform this omni-directional orientation after going through the final bifurcation point to reach the lesion 23. During this rotation, the bendable medical device 3 can rotate the bending plane of only the first bendable segment 12 without moving the second and the third bendable segments 13 and 14.

The second maneuver is a clustering sampling, as provided in FIG. 3c. The first bendable segment 12 can dislocate the position of the distal end while keeping the orientation of the distal end. With this maneuver, the distal end can access the different positons in the lesion 23. The advantage of this maneuver is to access different positions in the lesion 23, or to perform fine adjustment of the position of distal end. The bendable medical device 3 can dislocate the distal end with the identical orientation. Therefore, the resolution (and accuracy/precision) of the positioning is directly related to the dislocation of the distal end.

Figure 4A:
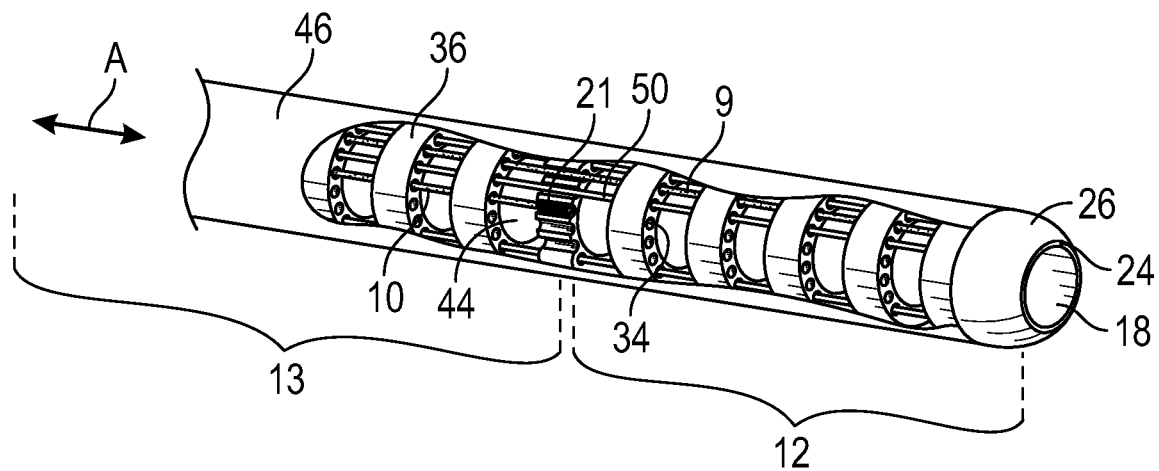
FIG. 4a provides a cut-away perspective view of an exemplary bendable medical device, according to one or more embodiment of the subject apparatus, method or system.
Figure 4B:
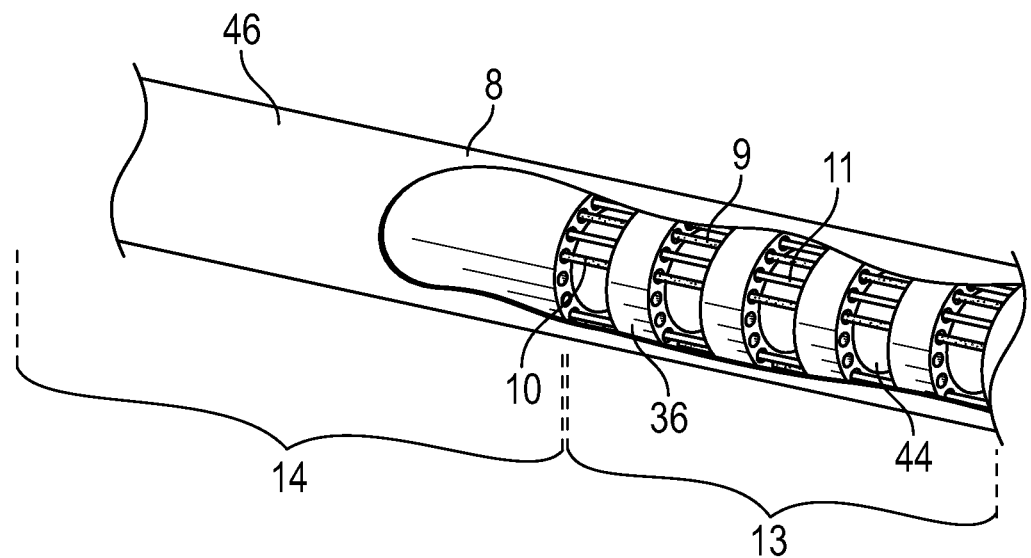
FIG. 4b is a close-up cut-away perspective view of an exemplary bendable medical device, according to one or more embodiment of the subject apparatus, method or system.
Figure 5:
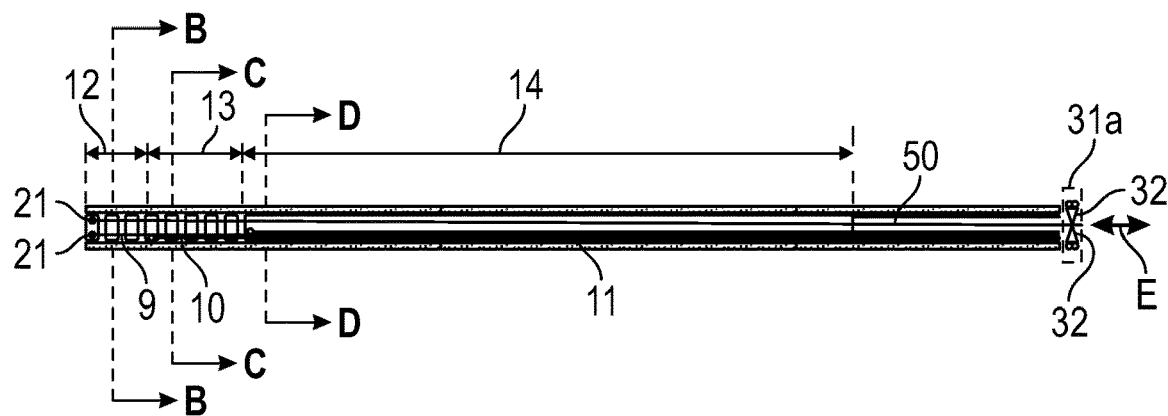
FIG. 5 provides a side perspective view of an exemplary bendable medical device, according to one or more embodiment of the subject apparatus, method or system.

As depicted in FIGS. 4a and 4b, the bendable medical device 3 includes a bendable body 7, wherein at least a portion of the structure of the bendable body 7 comprises multiple wire guides 36, wherein the wire guides 36 are configured a distance apart from one another and do not contact one another. The wire guides 36 are held in place by the cylindrical wall 8, which comprises an inner lining 44 and an outer lining 46, which provides bendable support to the bendably body 7 while retaining the wire guides 36 in a constant position along the axial direction of the bendable body 7. The inner lining 44 creates an inner diameter 40 and the outer lining 46 creates an outer diameter 42, wherein the inner diameter 40 establishes a tool channel 18. The edge of the bendable body 7 may be rounded by an atraumatic tip 26, to further diminish any harm to the internal elements of a patient as the bendable body 7 is advanced.

The adjacent guide rings 36, are attached to the inner lining 44 and outer lining 46, with cavities 30, created between the adjacent guide rings 36, distributed along the longitudinal direction of the bendable body 7. When bendable body is bent, the cavities 30 create evenly distributed wrinkles 60 (see FIG. 8a) in both the inner lining 44 and outer lining 46. Therefore, the cavities 30 avoid fatal kinking which may crush the tool channel 18 even when the bending sections 12 and 13 include thin total wall thickness.

In the depicted embodiment, the first bendable segment 12 and second bendable segment 13 incorporate wire guides 36 to provide structural support to the bendable medical device 3, while the third bendable segment 14 incorporates a more conventional wall without any gaps. The subject innovation is not limited to this particular embodiment, and the use of wire guides 36 may be used in any section, in whole or partially, within the bendable body and/or bendable medical device 3. For instance, the wire guides 36 may be used in the first bendable segment 12 and third bendable segment 14, with the second bendable segment 13 incorporating wire guides in limited part.

Each wire guide 36 contains at least two lumens 34, for slideable housing of the control wires 9-11, and is further configured to accept an anchor 21, which is displaced at the end of the control wires 9-11, to be embedded into the wire guides 36. In FIG. 4a, control wire 10 depicts the anchor 21, configured at the distal end of the second bendable segment 13. The space between adjacent wire guides 36, in cooperation with the resilient inner lining 44 and outer lining 46, allows the bendable body 7 to achieve a greater range of bending motion due to the open space between the wire guides 36, without kinking.

The tool channel 18 is configured to extend the length of the bendable body 7, wherein the proximal part 19 of the bendable body 7 provides access to clinical users for inserting/retreating a medical tool. For example, a clinical user can insert and retrieve a biopsy tool trough the tool channel 18 to the distal end 24 of the bendable medical device 3.

Figure 6A:
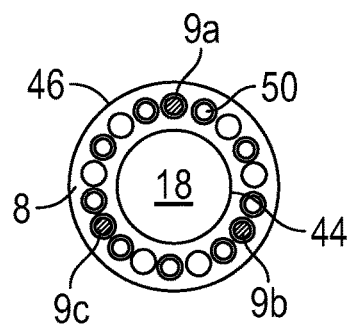
FIG. 6a depicts a cross-sectional view of an exemplary bendable medical device, according to one or more embodiment of the subject apparatus, method or system.
Figure 6B:
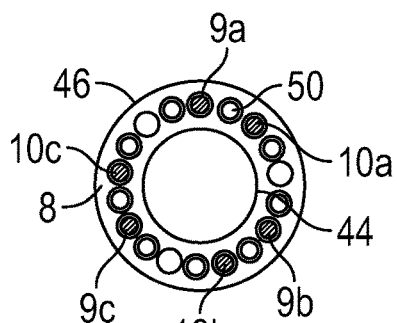
FIG. 6b provides a cross-sectional view of an exemplary bendable medical device, according to one or more embodiment of the subject apparatus, method or system.
Figure 6C:
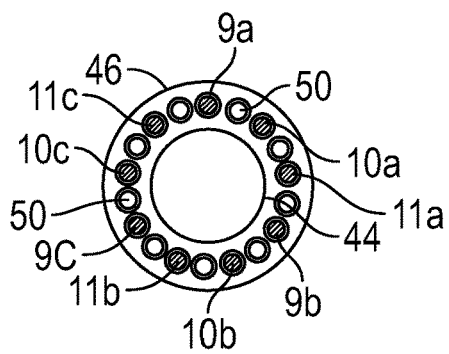
FIG. 6c depicts a cross-sectional view of an exemplary bendable medical device, according to one or more embodiment of the subject apparatus, method or system.

FIGS. 6a through 6c depict cross-sectional views of exemplary bendable medical devices shown in FIG. 5, according to one or more embodiment of the subject apparatus, method or system. FIG. 6a depict the cross-section view at the "B" line in FIG. 5, while FIG. 6b depicts the cross-sectional view at the "C" line, while FIG. 6c shows us the cross-sectional view at the "D" line of FIG. 5.

The bendable body 7 includes a set of first control wires 9a, 9b, 9c, a set of second control wires 10a, 10b, 10c, and a set of third control wires 11a, 11b, 11c housed in the wall 8, wherein each of the set of control wires 9, 10 and 11, corresponds to the first, second and third bendable segments 12, 13 and 14, respectively. The cylindrical wall 8 is formed by an inner lining 44 and an outer lining 46 which are congruent and combine with one another at the distal end 24 to encapsulate and form the wall 8. The wall 8 provides bendable support to the bendably body 7 while retaining the wire guides 36 in a constant position along the axial direction of the bendable body 7. The inner lining 44 creates the inner diameter 40 of the wall and establishes the tool channel 18, while the outer lining 46 creates the outer diameter 42 of the bendable body 7.

The wall 8 houses each of the control wires 9a-11c in corresponding lumens 34, configured along the longitudinal direction of the bendable body 7. The lumens 34 allow for slideable movement of the control wires 9a-11c along an axial direction of the bendable body 7. The control wires 9a-11c are terminated at the distal end of each bendable segments 12, 13 and 14, and form three groups with three wires each (a, b, c). The first control wires 9a, 9b, 9c are terminated at the distal end of the first bendable segment 12 with anchors 21, and are configured apart from each other by approximately 120 degrees within the wall 8. The first control wires 9a, 9b, 9c are connected to the driving unit 2 at the proximal end of the wires 9a, 9b, 9c. The driving unit 2 induces pushing or pulling forces to move the control wires 9a, 9b, 9c by actuating those wires, and bends the bendable body 7 from the distal end 24. The second control wires 10a, 10b, 10c and third control wires, 11a, 11b, 11c are similarly configured for their corresponding bendable segments 13 and 14, respectively.

Accordingly, by pushing and pulling the control wires 9a through 11c the first, the second and the third bendable segments 12, 13, 14, respectively, can individually bend the bendable medical device 3, in all three dimensions.

The subject bendable medical device 3 incorporates control wires 9, 10, 11, that can be fixed to the bendable body 7 by using minimal space in the bendable body wall 8. Because the anchors 21 are localized within the individual lumens 34, the bendable medical device 3 with the control wires 9, 10, 11, can be miniaturized effectively, especially when using multiple control wires 9, 10, 11. Additionally, the control wires 9, 10, 11, can be fully contained within the bendable body 7 wall 8, not needing to be outside the outer diameter 42 or inside the inner diameter 40; thus not impinging on the tool channel 18 or unnecessarily increasing the size of the medical device 3. By embedding the anchors 21 in the wall 8 of the bendable body 7, the control wires 9, 10, 11, can transmit pushing force, torque as well as pulling force to the bendable body 8. Therefore, the bendable medical device 3 can reduce the number of control wires 9, 10, 11, or force load per the control wire 9, 10, 11, to achieve the target bending maneuver in comparison to the conventional tendon-driven system with pulling forces.

Further depicted in FIGS. 6a through 6c are support wires 50 provided in the wall 8 of the bendable body 7. The support wires may provide added structural support to the wall 8 and may be anchored to the distal end 24 of a bending segments 12-14. The support wires 50 may run through lumens 34 configured in the wall 8, which may originate at the proximal part 19 of the bendable medical device 3. In certain embodiment, the support wires 50 may be configured for adjustable structural support of the wall 8. Exemplary adjustments for support may include employing various tensile strengths, configurations, resiliency of the support wires 50. In one embodiment, multiple support wires 50 may extend from the distal end 24 of the bendable medical device 3 to the proximal part 19 of the bendable medical device 3, thus allowing all segments 12-14 of the bendable body 7 to gain the kink prevention benefits.

Figure 7:
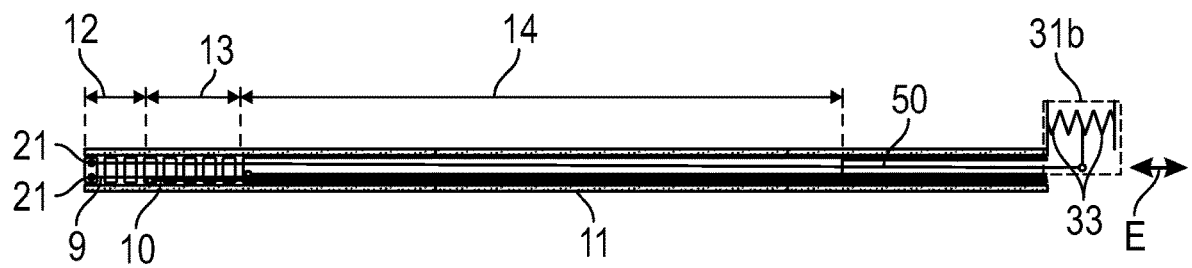
FIG. 7 illustrates a side perspective view of an exemplary bendable medical device, according to one or more embodiment of the subject apparatus, method or system.

FIGS. 5 and 7 provide side perspective views of exemplary bendable medical devices, according to one or more embodiment of the subject apparatus, method or system. FIG. 5 provides one example where the proximal end of the support wire 50 is attached to a proximal termination structure 31a. The proximal termination structure 31a is a slider element 32 that supports the support wire 50 slideably. Therefore, the support wire 50 would not be subjected to the tension and contraction forces when the bendable body 7 is bended, and minimize additional bending rigidity.

FIG. 7 is another embodiment, wherein a proximal termination structure 31b having a spring element 33. The support wires 50 are elastically terminated at the proximal termination structure 31b, and provide restoring force without increasing wall thickness.

Figure 8A:
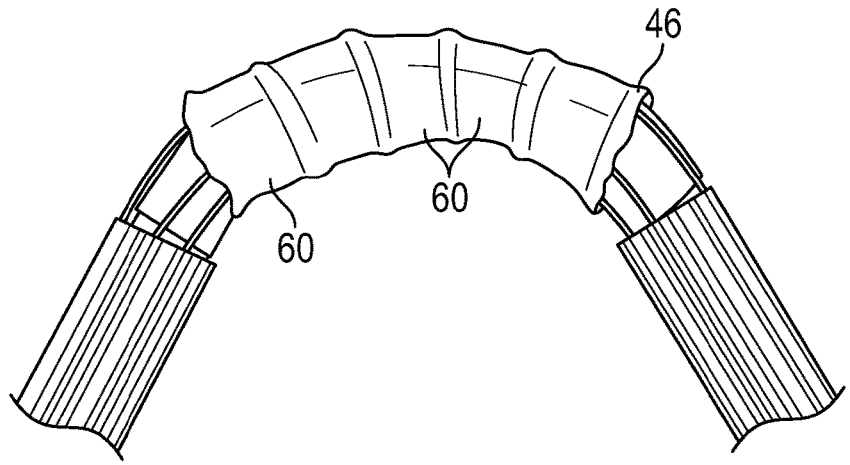
FIG. 8a provides a photograph of an exemplary bendable medical device, according to one or more embodiment of the subject apparatus, method or system.
Figure 8B:
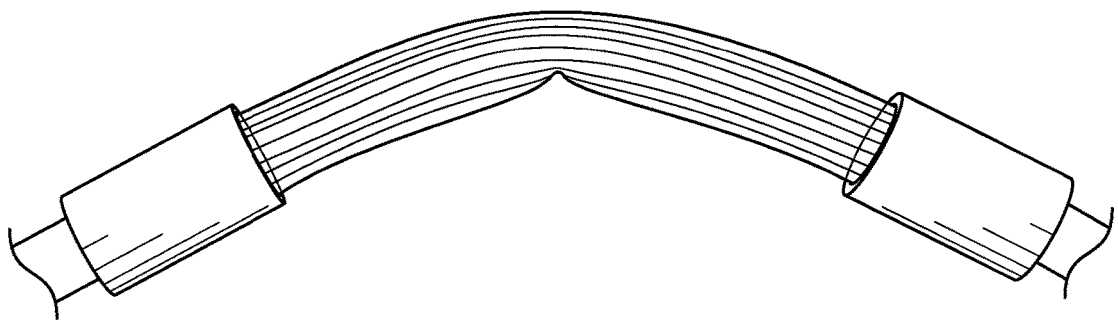

In FIG. 8a is a photo detailing the subject bendable medical device, while FIG. 8b is a photo of a conventional medical bending device, wherein both photos show the device bent, for comparison purposes. As depicted, FIG. 8b shows the fatal kinking with the conventional tubular sheath as taught by the prior art. Whereas, FIG. 8a shows the subject medical bending device which allows for even distribution of the bend without any kinks. The wrinkling shapes of the cylindrical outer wall 46 with the bendable body 7 of the subject innovation avoids fatal kinking while allowing for a greater bending angle than the prior art.

The invention claimed is:

1. A medical apparatus comprising:
   a bendable body having a hollow chamber extending a length thereof;
   at least two guide rings disposed in the bendable body, and spaced a distance from one another to define first and second opposite sides of a cavity;
   at least two lumens in the bendable body, the at least two lumens extending the length of the bendable body and parallel with at least a portion of the hollow chamber;
   at least one control wire slideably situated in at least one lumen of the at least two lumens and attached to a distal end of the bendable body; and
   a wall extending along the bendable body,
   wherein the wall includes a resilient outer lining and a resilient inner lining that encapsulate the at least two guide rings to define third and fourth opposite sides of the cavity,
   wherein respective outside diameters of the at least two guide rings are affixed at respective positions of the wall of the resilient inner lining, and
   wherein the wall is pliable to allow for bending of the bendable body.

2. The apparatus of claim 1, wherein the bendable body has a first bendable section and a second bendable section, wherein the at least two guide rings are disposed in the first bendable section.

3. The apparatus of claim 1, wherein an inside diameter of the at least two guide rings are affixed to at least a portion of the wall.

4. The apparatus of claim 1, further comprising an actuator attached to a proximal end of the at least one control wire,
   wherein the actuator is configured to actuate the at least one control wire.

5. The apparatus of claim 1, further comprising a support wire slideably situated in the at least one lumen of at least one guide ring.

6. The apparatus of claim 5, wherein the support wire is attached to the bendable body at a distal end of the support wire.

7. The apparatus of claim 5, wherein the support wire extends through at the least two lumens, and
   wherein the at least two lumens are parallel to the hollow chamber.

8. The apparatus of claim 5, further comprising a plurality of support wires configured around the hollow chamber.

9. The apparatus of claim 5, wherein the support wire is configured to freely move within at least one lumen as the apparatus is manipulated.

10. The apparatus of claim 1, further comprising a second control wire slideably situated in at least one lumen and attached to the bendably body,
    wherein the position of attachment for the first and the second control wires are different along the axial direction of the bendable body.

11. The apparatus of claim 1, wherein the at least one control wire comprises a radio opaque material.

12. A medical apparatus comprising:
    a bendable body having a first bending section and a second bending section, with the first bending section in a position distal to the second bending section;
    at least two lumens in the bendable body extending the length of the bendable through the first bending section and second bending section;
    a first control wire connected to a distal end of the first bending section;
    a second control wire connected to a distal end of the second bending section;
    wherein the first bending section comprises:
        at least two guide rings disposed in the bendable body and spaced a distance from one another to define first and second opposite sides of a cavity; and a wall extending the length of the first bending section and affixed to the at least two guide rings, wherein the wall comprises a resilient outer lining and a resilient inner lining that encapsulate the at least two guide rings to define third and fourth opposite sides of the cavity, wherein either or both of the resilient inner lining or resilient outer lining is affixed to the at least two rings, wherein the first control wire is slideably situated in the lumen of the first bending section and the second control wire is situated in the lumen of the second bending section, and wherein the wall is pliable to allow for bending of the bendable body.

13. The apparatus of claim 12, wherein the first control wire and second control wire both terminate at an actuation unit capable of independently actuating each of the first control wire and second control wire.

14. The apparatus of claim 12, further comprising at least one support wire slideably situated in at least a portion of the bendable body.

15. The apparatus of claim 14, wherein the at least one support wire is attached to the bendable body at a distal end of the support wire.

16. The apparatus of claim 14, wherein the support wire extends through the at least two lumens, and
wherein the at least two lumens are parallel to a hollow chamber of the bendable body.

17. The apparatus of claim 14, further comprising a plurality of support wires configured around a hollow chamber of the bendable body.

18. The apparatus of claim 15, wherein the at least one support wire is configured to freely move within the lumen as the apparatus is manipulated.

19. A method for treating a subject, comprising:
providing a medical apparatus comprising:
a bendable body having a hollow chamber extending a length thereof;
at least two guide rings disposed in the bendable body, and spaced a distance from one another to define first and second opposite sides of a cavity;
at least two lumens in the bendable body, the at least two lumens extending the length of the bendable body and parallel with at least a portion of the hollow chamber;
at least one control wire slideably situated in at least one the lumen of the at least two lumens and attached to a distal end of the bendable body, and
a wall extending along of the bendable body,
wherein the wall includes a resilient outer lining and a resilient inner lining that encapsulate the at least two guide rings to define third and fourth opposite sides of the cavity,
wherein respective outside diameters of the at least two guide rings are affixed at respective positions of the wall of the resilient inner lining, and
wherein the wall is pliable to allow for bending of the bendable body;
advancing the medical apparatus into a subject;
bending the medical apparatus to accommodate obstacles in the subject; and
treating the subject once the medical apparatus advances to a desired target in the subject.

* * * * *